United States Patent
Moon et al.

(10) Patent No.: US 7,403,113 B2
(45) Date of Patent: Jul. 22, 2008

(54) GAN-BASED SENSOR NODES FOR IN SITU DETECTION OF GASES

(75) Inventors: Jeong-Sun Moon, Moorpark, CA (US); Nicholas Prokopuk, Ridgecrest, CA (US); Kyung-Ah Son, Moorpark, CA (US)

(73) Assignees: California Institute of Technology, Pasadena, CA (US); HRL Laboratories, LLC., Malibu, CA (US); The United States of America as represented by the Secretary of the Navy, Washington, DC (US)

( * ) Notice: Subject to any disclaimer, the term of this patent is extended or adjusted under 35 U.S.C. 154(b) by 209 days.

(21) Appl. No.: 11/128,110

(22) Filed: May 11, 2005

(65) Prior Publication Data
US 2005/0263790 A1    Dec. 1, 2005

Related U.S. Application Data

(60) Provisional application No. 60/592,513, filed on Jul. 29, 2004, provisional application No. 60/571,713, filed on May 17, 2004.

(51) Int. Cl.
*G08B 1/08*    (2006.01)

(52) U.S. Cl. .............................. 340/539.22; 340/686.1; 340/539.1; 340/533; 73/24.06; 73/23.35

(58) Field of Classification Search ............ 340/539.22, 340/539.17, 539.21, 539.1, 533, 539.27, 340/539.13, 686.1; 73/23.2, 24.06, 23.35
See application file for complete search history.

(56) References Cited

U.S. PATENT DOCUMENTS

| | | | | |
|---|---|---|---|---|
| 4,365,238 A | * | 12/1982 | Kollin | 340/521 |
| 5,683,569 A | * | 11/1997 | Chung et al. | 205/775 |
| 6,057,773 A | * | 5/2000 | Shukla et al. | 340/623 |
| 6,168,962 B1 | * | 1/2001 | Itoh et al. | 438/22 |
| 6,489,628 B1 | * | 12/2002 | Morizuka | 257/12 |
| 7,053,439 B2 | * | 5/2006 | Kan et al. | 257/315 |
| 2004/0121354 A1 | * | 6/2004 | Yazawa et al. | 435/6 |
| 2005/0153276 A1 | * | 7/2005 | Wikswo et al. | 435/5 |
| 2006/0163594 A1 | * | 7/2006 | Kuzmik | 257/94 |

FOREIGN PATENT DOCUMENTS

DE    B 87 (2002) 425-430    *    8/2002

OTHER PUBLICATIONS

J. Schalwig Gas sensitive GaN/AlGaN-heterostructures Apr. 24, 2002 B 87 (2002) 425-430.*

Neuberger, R., et al., "High-Electron-Mobility AlGaN/GaN Transistors, HEMTs) for fluid Monitoring Applications", *Phys Status Solidi A* 185, 85 (2001).

(Continued)

*Primary Examiner*—George A Bugg
*Assistant Examiner*—Daniel Previl
(74) *Attorney, Agent, or Firm*—Steinfl & Bruno

(57) ABSTRACT

A system for detecting chemical/biological substances and a detection method. The system comprises a plurality of sensing units or nodes and a radiofrequency link. Each unit has several sensors with different sensing curves. Each sensor is able to transmit information related to the sensed substance on a specific frequency. The sensors preferably comprise AlGaN/GaN high electron mobility transistors.

29 Claims, 6 Drawing Sheets

OTHER PUBLICATIONS

Pearton, S.J., et al., "GaN-based diodes and transistors for chemical. Gas biological and pressure sensing", *Journal of Physics:Condensed Matter 16*, R961-R994 (2004).

Schalwig, J., et al., "Gas Sensitive GaN/ AlGaN heterostructures", *Sensors and Acuators B-Chemical*, 87(3). pp. 425-430 (Dec. 20, 2002).

Schalwig, J., et al., "Group III-Nitride-based Gas Sensors for Combustion Monitoring", *Materials for Science and Engineering, Solid State Materials for Advanced Technology*, 93 (1-3), pp. 207-214 (May 30, 2002).

Son, K., et al., "Gas Phase Atomic Hydrogen-Induced Hydrogenation of Cyclohexene on the Ni (100) Surface", *Journal of Physics and Chemistry*, 101 (18) pp. 3450-3546 (1997).

Stutzman, M., et al., "GaN-based heterostructures for applications", *Diamond and Related Materials*, 11(3-6) pp. 886-891 (Mar.-Jun. 2002).

\* cited by examiner

GAN-BASED SENSOR NODES FOR IN SITU DETECTION OF GASES

CROSS-REFERENCE TO RELATED APPLICATIONS

This application claims the benefit of U.S. provisional Patent Application Ser. No. 60/571,713, filed May 17, 2004 for "Temperature Controlled and Gate Metal Specific AlGaN/GaN HEMT Arrays for Robust Highly Selective and Sensitive Chemical Sensors" by Kyung-Ah Son, Jeong S. Moon and Nicholas Prokopuk and the benefit of U.S. provisional Patent Application Ser. No. 60/592,513, filed Jul. 29, 2004 for "Wireless GaN-Based Microsensor Node for Sensor Centric Networks" by Kyung-Ah Son, Jeong S. Moon and Nicholas Prokopuk, the disclosure of all of which is incorporated herein by reference.

STATEMENT REGARDING FEDERALLY SPONSORED RESEARCH OR DEVELOPMENT

The present invention described herein was made in the performance of work under a NASA contract, and is subject to the provisions of Public Law 96-517 (35 USC 202) in which the contractor has elected to retain title.

BACKGROUND

1. Field

The present writing is directed to GaN-based sensor nodes for in situ detection of gases.

2. Related Art

The AlGaN/GaN hetero structures contain polarization sheet charges (i.e. a two dimensional electron gas) at the interfaces due to differences in the piezoelectric effect of AlGaN and GaN. These polarization charges respond very sensitively to the exposure to polar liquids and gas molecules. In the AlGaN/GaN high electron mobility transistors (HEMT), the ions created by the reaction of chemical molecules with the transition metal contacts induce significant effects on the electrostatic surface termination of the nitride and thus influence the barrier height of the Schottky contacts. In fact, several experimental results published in recent literature indicate that AlGaN/GaN HEMT has a strong potential for chemical sensor. See, for example, "Gas Sensitive GaN/AlGaN-heterostructures" by Schalwig J, Muller G, Eickhoff M, Ambacher O, Stutzmann M, Sensors and Actuators B-Chemical, 87 (3): 425-430 Dec. 20 2002; "Group III-nitride-based Gas Sensors for Combustion Monitoring" by Schalwig J, Muller G, Eickhoff M, Ambacher O, Stutzmann M, Materials Science and Engineering B-Solid State Materials for Advanced Technology, 93 (1-3): 207-214 May 30, 2002; "GaN-based heterostructures for sensor applications" by Stutzmann M, Steinhoff G, Eickhoff M, Ambacher O, Nebel CE, Schalwig J, Neuberger R, Muller G, Diamond and Related Materials, 11 (3-6): 886-891 March-June 2002; "High-Electron-Mobility AlGaN/GaN Transistors, (HEMTs) for Fluid Monitoring Applications" by Neuberger R, Muller G, Ambacher O, Stutzmann M, Phys. Status Solidi A 185, 85 (2001); and "GaN-based diodes and transistors for chemical. Gas biological and pressure sensing" by Pearton S. J., Kang B. S., Kim S., Ren F., Gila B. P., Abernathy C. R., Lin J., Chu S. N. G., J. Phys.: Condens. Matter 16 (2004) R961-R994.

However, a limitation of AlGaN/GaN hetero structure devices, similar to other chemical sensing FETs (field effect transistors), is poor selectivity in chemical detection. The low selectivity in chemical detection is a major hurdle to practical approach.

Further, a majority of the current stand-off or remote chemical detection/monitoring systems are based on optical/IR spectral analysis and deployed on mobile platforms. These systems offer excellent chemical identification capability but are large, expensive, and require long data acquisition times.

Another major drawback of optical/IR systems is that functionality can be dramatically reduced in bad weather/fog due to undesirable signal attenuation. In addition, for the safety and security of the end users, real-time and autonomous monitoring of the continuously changing chemical environment using remote sensing networks is also very important.

SUMMARY

According to a first aspect, a detection system is provided, comprising: a plurality of sensing units, each unit comprising a plurality of transistor-based sensors, each sensor having a different sensing characteristic from the other sensors; and a radiofrequency link, to allow transmission of sensor signals from the sensors to a receiving unit.

According to a second aspect, a detection method is provided, comprising: providing at least one sensor node, the sensor node comprising a plurality of sensors, each sensor having a first signal output if a substance is sensed and a second signal output if a substance is not sensed; allocating a transmission frequency to each sensor; and providing a transmitter to transmit a transmission signal indicative of the first or second signal output around the transmission frequency of one of the sensors.

According to a third aspect, a detection method is provided, comprising: providing a plurality of transistor-based sensors, each sensor adapted to detect a specific chemical or biological species; and characterizing the chemical or biological species by a desorption temperature profile of the species on a material provided with each sensor.

According to a fourth aspect, a detection method is provided, comprising: providing a plurality of transistor-based sensors, each transistor-based sensor adapted to detect a specific chemical or biological species in a detection medium; locating the transistor-based sensors on one or more sensing nodes; operating each sensor at a specific temperature; and providing a radiofrequency link to allow transmission of sensor signals from each of said one or more sensing nodes to a receiving unit.

The approach according to the present disclosure enables highly selective and sensitive AlGaN/GaN micro chemical sensors that can operate in wide temperature and pressure ranges and in harsh environments.

Further, the approach according to the present disclosure allows to overcome the limitations of the current stand-off or remote detection technologies by making GaN-based microsensor nodes that are constructed with high sensitivity and specificity AlGaN/Gan HEMT-based chemical sensor arrays and an RF link for molecule-specific RF tagging and data transmission.

The AlGaN/GaN sensors system described herein enable in situ detection of gases and temperatures and pressures in planetary atmospheres under extreme conditions and are a powerful tool to study deep planetary atmospheres during future missions, in particular in situ exploration of Venus and the giant planets.

Sensitivity of HEMT or FET-based devices is generally high in view of the fact that the electron channel of those devices is close to their surface, with a distance of about 10 nm. Sensitivity in AlGaN/GaN HEMT sensors is even higher because of their surface polarization.

DETAILED DESCRIPTION

Figure 1:
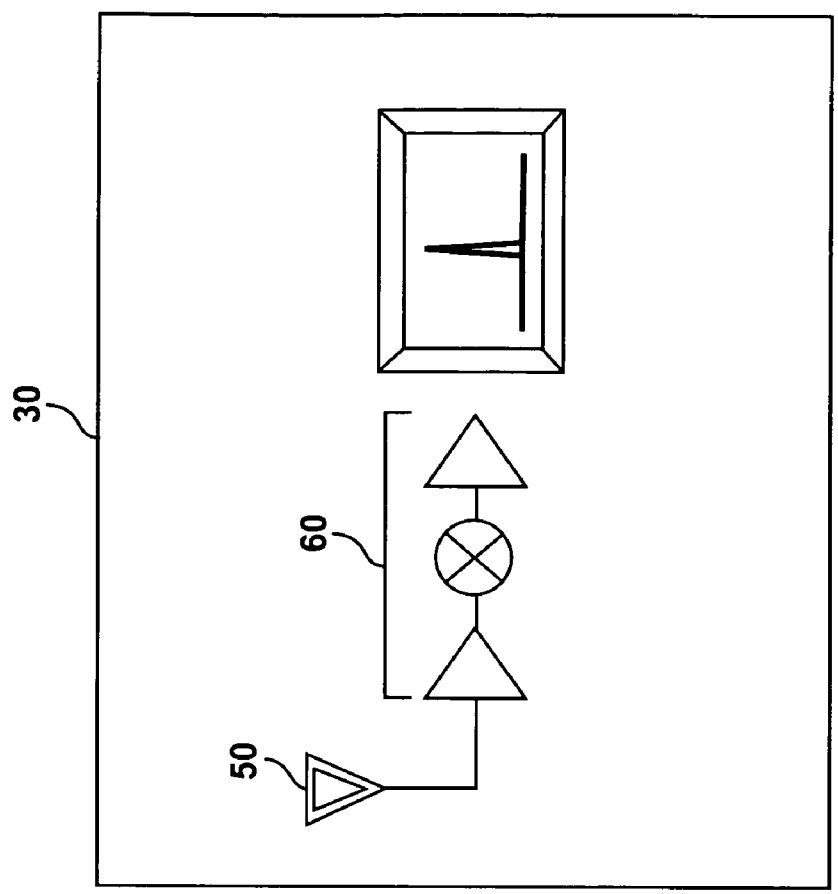
FIG. 1 shows a schematic representation of the system in accordance with the present disclosure.
Figure 1:
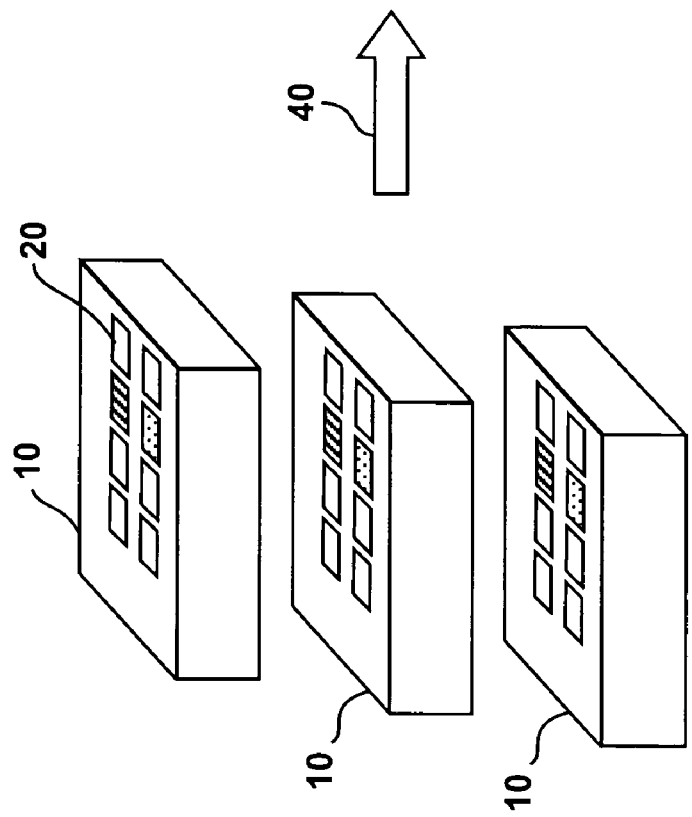

FIG. 1 shows a schematic representation of the system in accordance with the present disclosure.

FIG. 1 shows distributed units 10 of AlGaN/GaN HEMT chemical sensor arrays. Each unit 10 comprises an array of sensors 20. Each sensor 20 has a sensing curve that is different from the sensing curve of other sensors in the array. In this way, each unit 10 can sense a plurality of different chemical molecules and/or compounds in the environment where the unit is placed.

In accordance with the present disclosure, selectivity in chemical/gas detection of the sensors according to the present disclosure is provided by (1) employing an array of AlGaN/GaN HEMT sensors that are optimized for the detection of specific chemical species and (2) by taking temperature desorption spectroscopy of each HEMT sensor.

In accordance with the first prong described above, optimization for the detection of specific chemical species means the AlGaN/GaN HEMT sensors of the array are fabricated with a range of gate metals (preferably catalytically active transition metals such as Pt, Pd, Ir, Ni, Mo and W, or also metals such as Cu, Ru and Rh) that are selected for the most efficient ionization of target chemical species. In particular, adsorption of chemical species on the gate electrode creates surface ions, which subsequently modulate the 2DEG channel current in the sensor. Therefore, depending on the catalytic characteristics of the gate metal, the sensor's response to a specific chemical species varies significantly.

In accordance with the second prong described above, in order to further enhance the specificity of the sensor, a novel chemical sensing mechanism based on temperature-dependent desorption spectroscopy is used. In particular, each chemical species is characterized by a desorption temperature profile. Each transition metal gate has a specific surface interaction mechanism with its target chemical, resulting in characteristic adsorption coefficients and adsorption/desorption temperatures. In the approach according to the present disclosure, the identify of an analyte is determined by these properties, and detected as an electrical response, i.e. the change in 2DEG channel conduction of the HEMT devices as a function of temperature. In order for this prong to operate properly, sensors able to tolerate higher temperature operation should be used. AlGaN/GaN sensors represent a preferred choice for the sensors to be used in accordance with the present disclosure.

Figure 2:
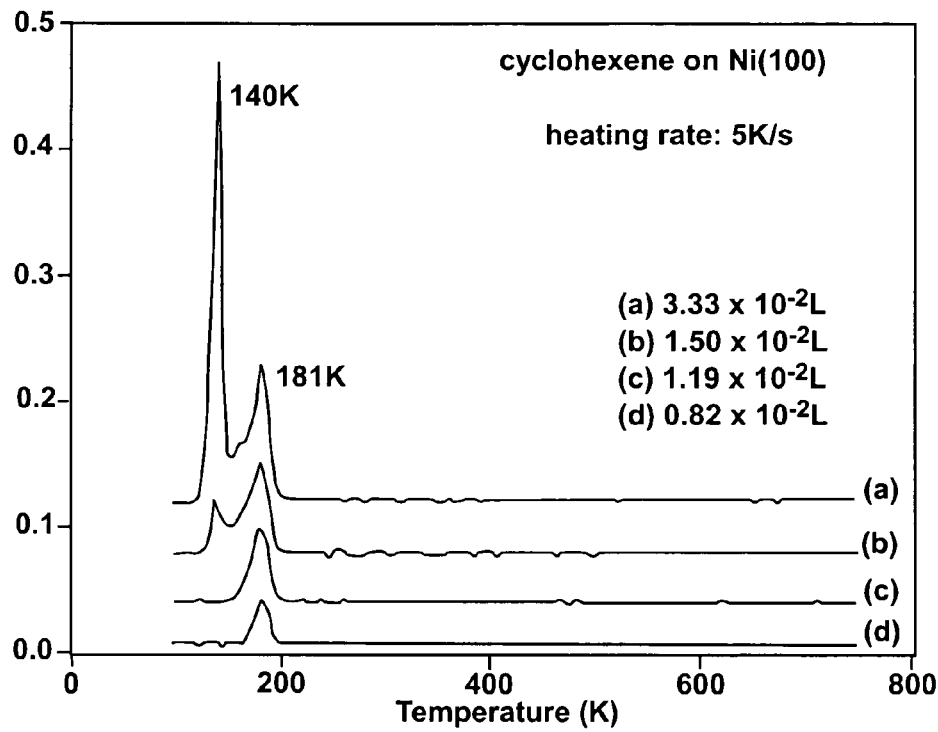
FIGS. 2 and 3 show temperature desoprtion spectroscopy diagrams of cyclohexene and benzene adsorbed on a Ni surface.
Figure 3:
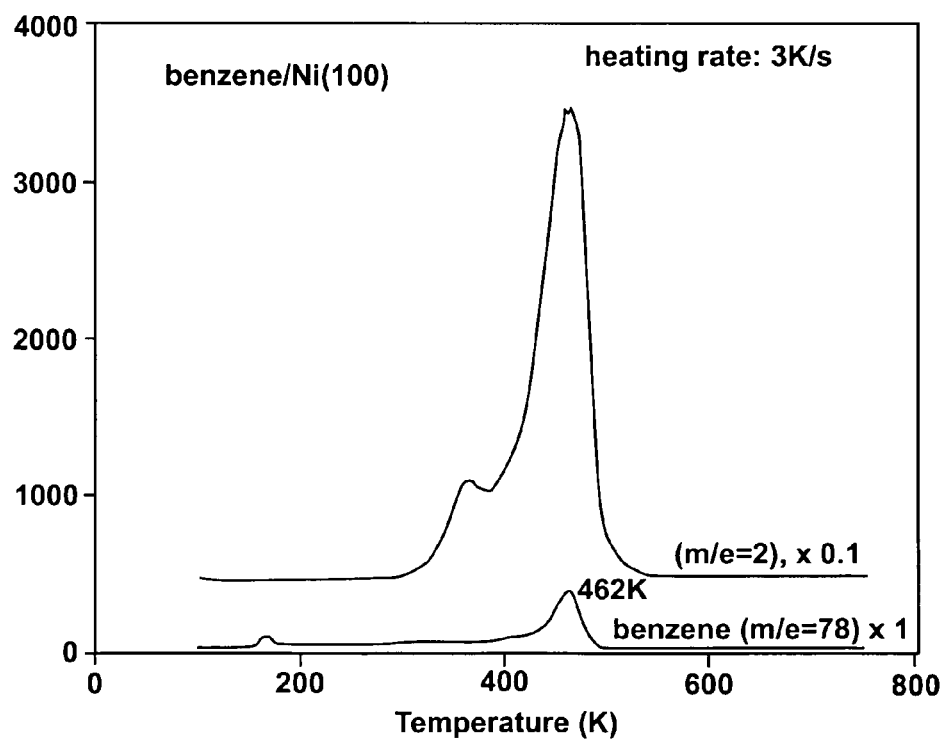

Similarly to thermal desorption spectroscopy (TDS), responses are measured as a function of temperature. In particular, TDS detects molecules desorbing from the surface while a termal ramp is applied, using a mass spectrometer. For example, FIGS. 2 and 3 show TDS of cyclohexene ($C_6H_{10}$) and benzene ($C_6H_6$) adsorbed on a Ni surface. See Gas Phase Atomic Hydrogen-Induced Hydrogenation of Cyclohexene on the Ni(100) Surface by Son, Kyung-ah and Gland, J. L., *J. Phys. Chem. B.* 1997, 101(18), 3540-3546, which is incorporated herein by reference in its entirety.

The molecules desorbing from the Ni surfaces were detected by a quadrupole mass spectrometer using 70 eV ionization energy. With reference to FIG. 2, desorption of monolayer and multiple layers of cyclohexene occur at 181 K and 140 K, respectively.

With reference to FIG. 3, benzene is more strongly bound to the Ni surface primarily due to the electrons in its π orbital and therefore desorbs from the surface at a higher temperature of 462 K. The spectrum of m/e=2 is mostly due to the fragments of benzene produced in the mass spectrometer. Therefore, despite similar molecular weights, benzene makes a stronger bonding to a Ni surface compared to cyclohexene and consequently desorbs from Ni surfaces at much higher temperatures.

The applicants, starting from the above results, have noted that different surface interactions between transition metal surfaces and adsorbing molecules can be used in order to detect and identify specific analytes.

In particular, according to the present disclosure, modulation of the 2DEG channel is measured in the HEMT as a function of temperature. Modulation of the 2DEG channel is caused by changing surface interactions of analyte molecules with the gate with temperature. By applying a thermal ramp to a sensor array, a library of gate metal-specific desorption profiles of each analyte is obtained. Such library is used for the identification of analytes ("fingerprinting") during operation of the sensors. In other words, using the desorption profile library acquired with the approach according to the present disclosure, the sensor array can be operated at a certain temperature range in order to separate the effect of one analyte from the other.

In the preferred embodiment of the present disclosure, for high selectivity and sensitivity chemical species detection, the applicants employ an array of HEMT sensors fabricated with a wide range of optimized metal gates that are selected based on their reaction characteristics. The electrical response (current-voltage and capacitance-voltage measurements) of each sensor in the array is then obtained as a function of temperature in order to generate the individual desorption spectrum for each individual species. According to a first approach, thermal desorption spectra of each sensor in the array are obtained during operation in the field and compared with the data library acquired before sensor deployment, to identify the analytes in the detection medium. According to an alternative approach, the sensor node can be operated at a specific temperature to sense a specific target chemical species. The first approach is preferred, because, in the second approach, the effects of other chemical species cannot be completely excluded.

In other words, the electrical responses of an array of AlGaN/GaN sensors are mapped out as a function of temperature in order to "finger print" specific chemical species. The temperature desorption spectroscopy of several HEMT devices with different gate metals will enable identification of the gas or liquid to be detected.

The HEMT devices with different gate metals will enable identification of the gas. The preferred operational temperature of AlGaN/GaN sensors in accordance with the present disclosure is in the −200 C to 500 C range, where adsorption and desorption of all common chemicals occur. However, the person skilled in the art will understand that other temperatures and temperature ranges are possible.

Temperature and pressure sensitivities of AlGaN/GaN HEMT devices are characterized (i.e. measured and tested) in order to identify the sensors' responses to the chemicals alone.

The amount of each chemical present in the detection medium is based on current-voltage and capacitance-voltage measurements of the sensor.

Turning to FIG. 1, the units 10 are connected to a wideband receiver 30 by means of a wireless or radiofrequency (RF) link 40. The receiver 30 allows the location of the unit 10 to be detected, together with the particular sensing characteristic of one of the sensors 20 located on the unit 10.

The receiver 30 comprises a receive antenna 50 connected to a low noise amplifier (LNA) 60 to amplify the signal captured at the antenna 50. The receiver 30 will not be described in detail in the present disclosure, because it is well known as such to the person skilled in the art. The bandwidth of the receiver should be within the RF transmission spectra of the units 10.

The data signals transmitted by the units 10 are encoded by means of RF tagging. In other words, the detection signal transmitted by a sensor 20 is attached to a radiofrequency label, in order to allow the receiver 30 to understand which is the unit and the sensor (inside the unit) from which the detection signal is originated.

It should be noted that RF tagging is done with gas-specific or liquid-specific frequency allocation, which allows remote sensor systems to be fabricated without on-board signal processing units.

Each microsensor array node preferably incorporates one or more heating elements, such as microstrip heating elements (e.g. TaN or NiCr). These heating elements are microfabricated on the backside of the sensor substrate, e.g., using lithography, thin film deposition, dry etching or wet etching. Thin film deposition can occur, for example, with either electron beam evaporation or sputter deposition. For effective heating, materials with high thermal conductivity (e.g. SiC) are used as the substrate for the HEMT sensors. Temperature control can be done in several different ways such as (1) with on-chip feedback control, (2) pre-programmed heating, and (3) remote controlled heating. The presence of the heating elements allows thermal desorption spectroscopy to be obtained. One heating element common to all sensors can be provided, or, alternatively a plurality of heating elements.

Figure 13:
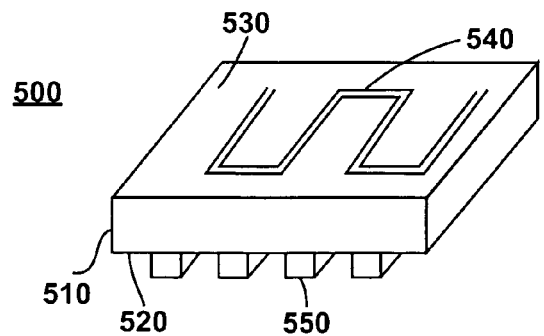
FIG. 13 shows an embodiment of a sensor node in accordance with the present disclosure, viewed from the back side.

FIG. 13 shows an exemplary embodiment of a sensor node 500 viewed from the back side. The sensor node 500 comprises a substrate 510 (made, for example, of SiC) having a front side 520 and a back side 530. Micro heating stripes 540 are fabricated on the back side 530. FIG. 13 also shows a plurality of sensors 550 located on the front side 520.

Temperature control of the micro stripes 540 can be obtained, for example, by means of on-chip feedback control, pre-programmed heating, or remote controlled heating. The simplest approach is the pre-programmed heating approach. The prototype sensor node can be tested prior to deployment in order to determine the power required to achieve each temperature point.

Remote monitoring of the sensor array temperature can be achieved using the output from one or more control, encapsulated HEMT devices in the array. Therefore, according to one embodiment of the present invention, both device sensing HEMT devices and temperature measurement HEMT devices are provided. Preferably, the control or temperature measurement HEMT devices will have gate metals and device structures that are identical to the chemical sensing HEMT devices. However the temperature measurement HEMT devices will be preferably hermetically sealed with an inert gas (e.g. Ar) to isolate them from the chemical species-containing ambient. The response of the chemical sensing HEMT detectors will then be compensated for solely temperature-related effects.

Figure 4:
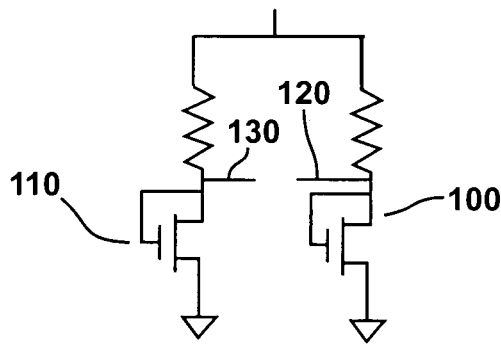
FIGS. 4-6 show a schematic representation of a preferred construction of each sensor and the behavior of each sensor before chemical exposure and during chemical exposure.
Figure 5:
Figure 6:
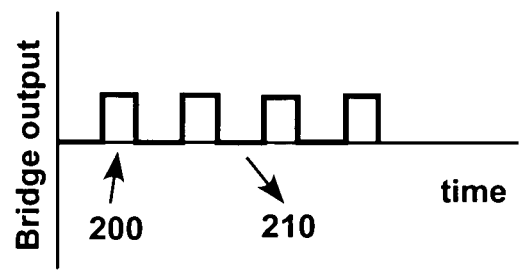

FIGS. 4-6 show a schematic representation of a preferred construction of each sensor 20 and the behavior of each sensor 20 before chemical exposure and during chemical exposure.

In particular, FIG. 4 shows an electrical circuit representation of the sensor 20, which comprises a sensing device portion or arm 100 and a reference device portion or arm 110. The reference device portion 110 is, for example, a device which is encapsulated in order not to be contaminated from the chemical molecules of the environment to which the sensor 20 is exposed. Therefore, the electrical behavior of the reference device portion 110 will not depend on the chemical molecules detected. On the other hand, the electrical behavior of the sensing device portion 100 varies in accordance with the chemical molecules detected. The electrical structure shown in FIG. 4 forms an RF-bridge circuit comprised in each of the sensors 20. Portions 100 and 110 are connected in a differential configuration. Preferably, the gate of transistor 110 is made of the same material of the gate of transistor 100. The differential output signal of the configuration of FIG. 4 is taken on the drains or collectors 120, 130.

RF communication is triggered when the sensor bridge of FIG. 4 is off-balanced due to chemical/biological gas sensing.

As already explained above, AlGaN/GaN-based HEMT transistors are a preferred embodiment for the sensors 20 of the present disclosure. However, any transistor-based sensor having high-temperature operability could be used.

FIG. 5 shows a time diagram of the RF-bridge output before chemical exposure. The horizontal axis of the diagram of FIG. 5 indicates time, while the vertical axis indicates the bridge voltage output. FIG. 6 shows a time diagram of the RF-bridge output during chemical exposure. Portions 200 of the waveform of FIG. 6 show a the bridge output signal when the sensor 20 is exposed to a chemical material. Portions 210 of the waveform of FIG. 6 show the bridge output signal when the sensor 20 is not exposed to a chemical material.

Figure 7:
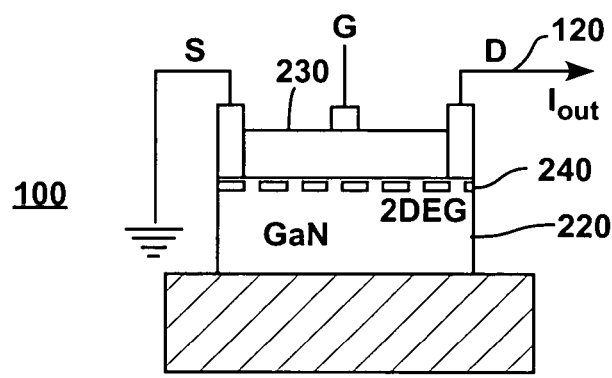
FIG. 7 shows a schematic representation of an AlGaN/GaN High Electron Mobility Transistor (HEMT).

FIG. 7 shows a schematic representation of an AlGaN/GaN High Electron Mobility Transistor (HEMT) to be used as a preferred embodiment for the transistor 100 in FIG. 4. The transistor 100 is well known as such and comprises a GaN layer 220 and an AlGaN layer 230. At the interface between layers 220 and 230 a mobile sheet charge layer (2DEG) 240 is generated, due to spontaneous and piezoelectric polarizations. According to the present disclosure, the binding of the chemical species modulates the electron concentration in the 2DEG layer.

RF tagging of the circuit shown in FIG. 4 is obtained by allocating a specific RF transmission frequency within an overall, broad RF band. In order to allocate a specific transmission frequency fx for each sensor 20, a local oscillator will be used to generate a narrowband RF signal centered at the specific tag frequency fx.

Figure 8:
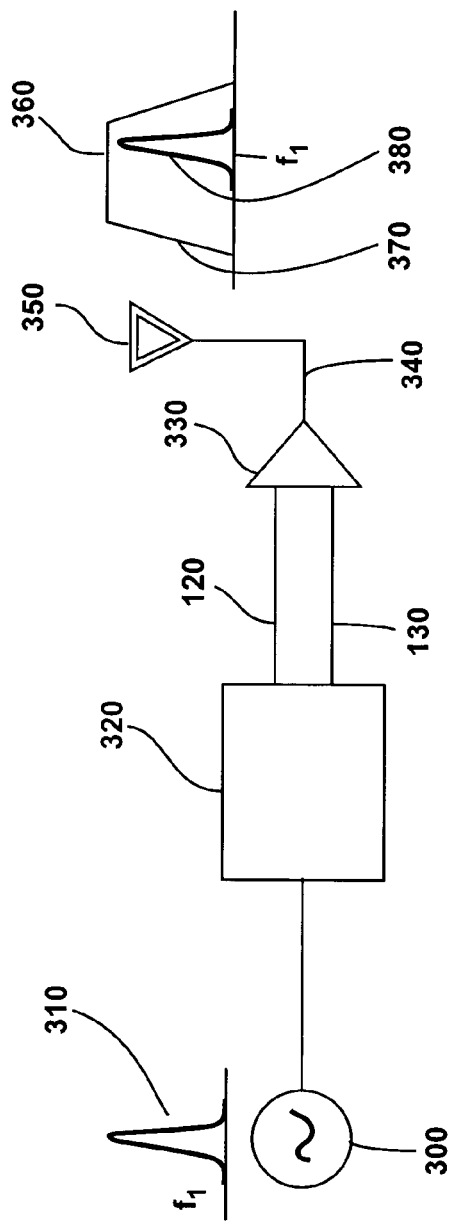
FIG. 8 shows an example of a circuitry to be connected to the RF bridge sensor to obtain RF tagging.

FIG. 8 shows an example of a circuitry to be connected to the RF bridge sensor to obtain RF tagging. A local oscillator 300 (preferably a high Q oscillator) having a frequency spectrum 310, for example a narrowband, less than 50 KHz frequency spectrum centered around frequency f1, is connected to an RF-bridge sensor 320 like the one shown in FIG. 4. The output 120, 130 of the RF-bridge sensor 320 is connected to a differential amplifier 330 whose output 340, in turn, is connected to a transmit antenna 350. The frequency spectrum of the output signal 340 will have a waveform 380 (narrowband, centered at f1 in the figure), which resides in the bandwidth 360 of the transmitting antenna 350.

Therefore, exposure of a sensor bridge (see FIG. 4) to a chemical/biological gas or liquid during a time window (see window 200 in FIG. 6) will output an RF signal centered at the local frequency of the oscillator (see frequency f1 of waveforms 310 and 380 of FIG. 8).

Figure 9:
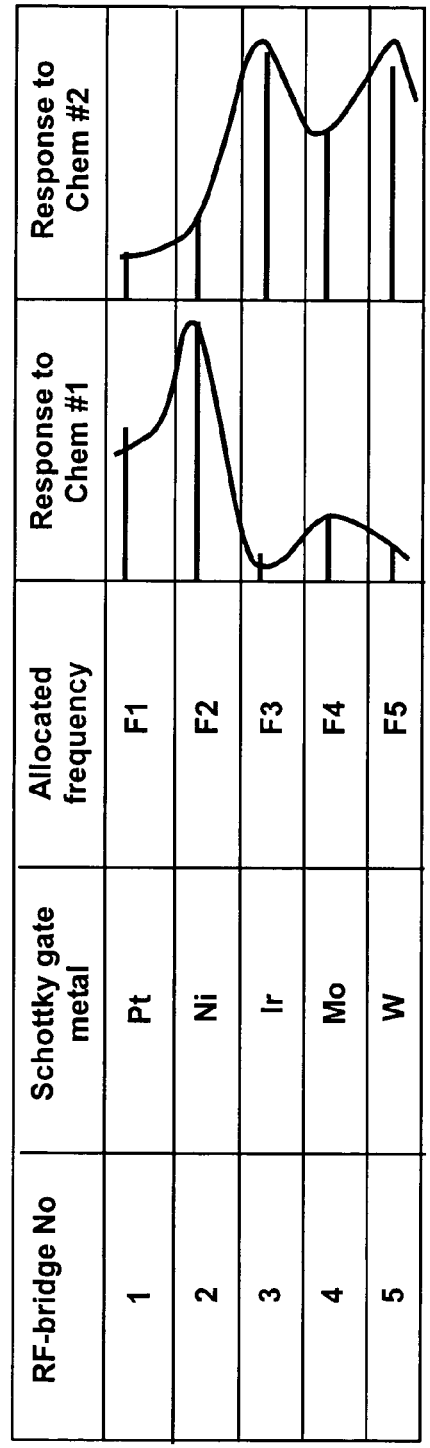
FIG. 9 shows a table with an exemplary mode of operation of the system in accordance with the present disclosure.

The table of FIG. 9 shows an exemplary mode of operation of the system in accordance with the present disclosure. Five different sensors 20 are shown, indicated in the first column of the table. The second column of the table indicates the material of which the gate of the transistor forming the sensing portion 100 of FIG. 4 is made. Sensor # 1 has a metal gate made of platinum (Pt). Sensor # 2 has a metal gate made of nickel (Ni). Sensor # 3 has a metal gate made of iridium (Ir). Sensor # 4 has a metal gate made of molybdenum (Mo). Sensor # 5 has a metal gate made of tungsten (W). The third column of the table indicates the frequency around which the oscillator 300 of FIG. 8 allocated to each RF-bridge oscillates. The fourth column of the table shows the differential voltage output 340 (see FIG. 8) of each sensor in response to a first chemical material or gas. The voltage response of each sensor will be different because the material of which each sensing gate is different. The fifth column of the table shows the differential voltage output of each sensor in response to a second chemical material or gas. Due to the different response of each gate metal to the chemicals or gases, unique responses are generated by the array of sensors 20 for each chemical or gas.

Collection of multiple sensor responses from different gate metals, as shown in FIG. 9, allows to compare the received sensor signal with a previously obtained built-in sensor database or library, as already explained before.

In order to allow the system according to the present disclosure to work in harsh planetary environments, robust sensors 20 are needed. Preferably, each unit 10 comprises an array of sensors 20 made of GaN high electron mobility transistors (GaN HEMTs). The GaN HEMTs are optimized for the detection of specific chemical materials or biogenic gases, i.e. gases produced by living organisms or biological processes. The person skilled in the art will understand that the sensors in accordance with the present disclosure can also be optimized to detect a broader range of chemical species (both biogenic and non-biogenic) in both gaseous and non-gaseous phases.

Catalytic transition metals have characteristic chemical bonding activation capability, which has been studied in surface chemistry for decades. The transition metals make interactions with molecules preferentially through specific chemical bonds (e.g., C—H, C—S or C—O) resulting in generation of different types and amounts of ions. Therefore, a proper gate metal can be selected for target chemical species for high selectivity and sensitivity detection. For example, Ni is known for being good at dissociating a C—H bond.

Figure 10:
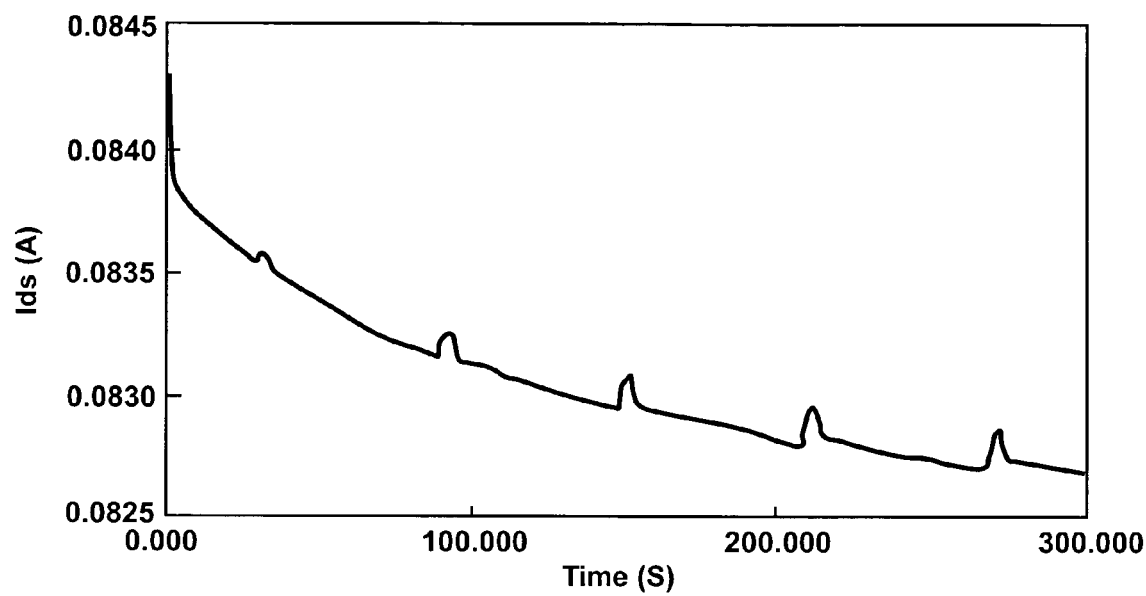
FIG. 10 shows the electrical response of a discrete GaN-based sensor to methane (CH4).

FIG. 10 shows the electrical response of a discrete GaN-based sensor to methane ($CH_4$). $CH_4$ is an important signature biogenic gas in the search for potential biospheres in our solar system, especially on Mars and Europa. In particular, FIG. 10 shows the source-drain current of a GaN HEMT sensor measured during exposure to $CH_4$. The test was performed in a room ambient condition. The sensor used for the test is an AlGaN (20% Al, 20 nm thick)/GaN (1 μm thick) HEMT fabricated using a Pt gate electrode (100 μm×100 μm). For these measurements the sensor was exposed to about 2 SLPM (standard liter per minute) for 5 seconds at about 1 minute intervals. While in this test no special effort was made to optimize the sensor for high selectivity to $CH_4$, the data clearly show an immediate increase of the source-drain current upon exposure to $CH_4$, thus indicating that the GaN device has a strong $CH_4$ sensitivity. In particular, immediate increase of source-drain current by up to 0.17 mA was measured, with a nominally unbiased gate voltage. Therefore, the test indicates that GaN sensors are very promising for in situ detection, monitoring and mapping of biogenic gases in the search for extraterrestrial life in extreme planetary environments. The person skilled in the art will understand that higher selectivity/sensitivity can be obtained once the effects of other gases (e.g. nitrogen, oxygen, water vapor) are minimized, for example, by controlling the operational temperature, selecting the gate electrode material, determining the AlGaN layer thickness, the AlN content in the AlGaN alloy, the geometry of the gate electrode, the distance between source and drain and so on.

Figure 11:
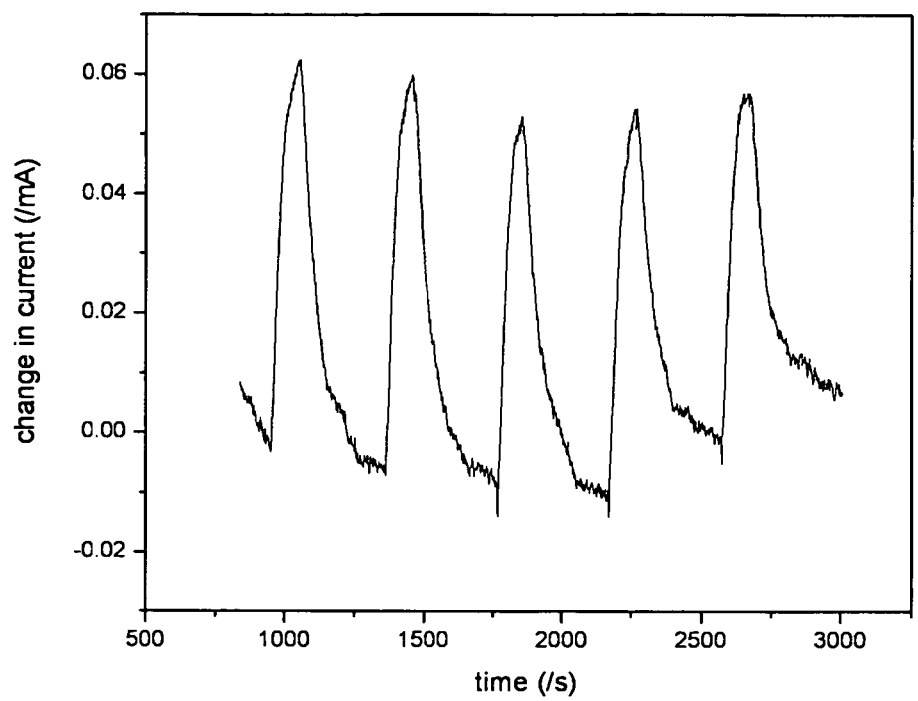
FIGS. 11 and 12 show the electrical response of an AlGaN/GaN HEMT sensor exposed to acetone and diethylcyanophosphonate, respectively.
Figure 12:
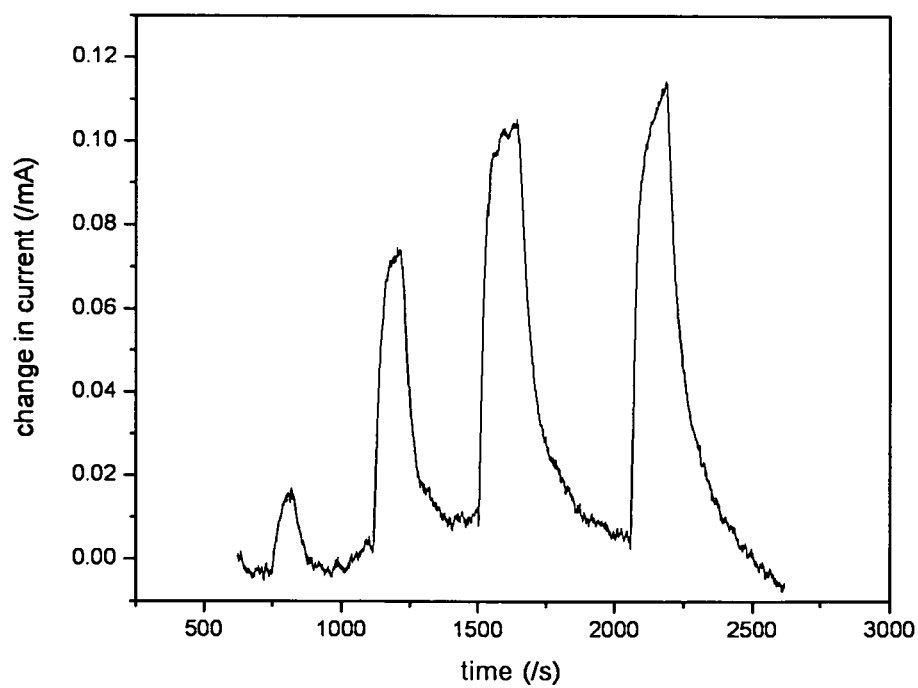

FIGS. 11 and 12 show the electrical response of an AlGaN/GaN HEMT sensor exposed to acetone and diethylcyanophosphonate, respectively. The source-drain current Ids was measured while the sensor was exposed to the gases diluted with nitrogen followed by pure nitrogen purge. The response to acetone measured with increasing concentration shows a corresponding increase of Ids. For the measurements, Vds=1.5 V and a nominally unbiased gate voltage were used, as an example.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art.

For example, although the disclosed "sensor+RF-link" concept has been described with reference to chemical/biological sensing, the person skilled in the art will understand that it can be applied to various sensor systems, for instance, for monitoring and mapping of wind speed temperature pressure in specific areas, such as a micro weather node.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

What is claimed is:

1. A detection system comprising: a plurality of sensing units, each sensing unit comprising a plurality of transistor-based sensors, each of the transistor-based sensors having a different sensing characteristic from the other transistor-based sensors, and each of the transistor-based sensors comprising different gate electrodes, said gate electrodes being optimized for detection and identification of a particular chemical species by way of a desorption temperature profile carried out by an operation selected from i) operating each sensor at a specific temperature and ii) applying a thermal ramp over a particular temperature range;
the detection system further comprising: a radio frequency link, to allow transmission of sensor signals from the sensors to a receiving unit.

2. The system of claim 1, wherein each transistor-based sensor comprises an AlGaN/GaN high electron mobility transistor.

3. The system of claim 1, wherein each gate electrode comprises a transition metal.

4. The system of claim 3, wherein the transition metal is selected from the group consisting of platinum, nickel, molybdenum, iridium, tungsten, palladium, ruthenium and rhodium.

5. The system of claim 1, further comprising the receiving unit.

6. The system of claim 5, wherein the receiving unit comprises a receiving antenna and a low noise amplifier connected to the receive antenna.

7. The system of claim 1, wherein the radio frequency link comprises frequency tagging means.

8. The system of claim 7, wherein the frequency tagging means comprises an oscillator connected to each sensor, wherein different oscillators have different oscillating frequencies.

9. The system of claim 1, wherein each sensor comprises a sensing portion and a reference portion, the sensing portion and the reference portion being arranged in a differential configuration.

10. The system of claim 9, wherein the sensing portion and the reference portion comprise an AlGaN/GaN HEMT.

11. The system of claim 10, wherein the sensing portion HEMT and the reference portion HEMT comprise a gate made of the same material.

12. The system of claim 1, wherein the system is for detecting a substance selected from the group consisting of: chemical substance, biological substance, gaseous-phase substance, and liquid-phase substance.

13. The system of claim 1, further comprising one or more heating elements.

14. The system of claim 13, wherein the one or more heating elements comprises heating micro stripes.

15. The system of claim 14, wherein the heating micro stripes are located on a back side of the system.

16. The system of claim 13, further comprising one or more temperature measuring devices, to measure a temperature of the sensing units.

17. The system of claim 16, wherein the one or more temperature measuring devices comprise HEMT devices.

18. A detection method comprising:
providing at least one sensor node, the sensor node comprising a plurality of sensors, each sensor having a first signal output if a substance is sensed and a second signal output if a substance is not sensed; each sensor comprising a sensing portion and a reference portion, the sensing portion and the reference portion being arranged in a differential configuration;
allocating a transmission frequency to each sensor; and
providing a transmitter to transmit a transmission signal indicative of the first or second signal output around the transmission frequency of one of the sensors.

19. The method of claim 18, wherein the transmitter is a radio frequency transmitter and the transmission signal is a radiofrequency signal.

20. The method of claim 18, further comprising: providing a receiver to receive the transmission signal.

21. The method of claim 18, wherein the method is for detecting a substance selected from the group consisting of: chemical substance, biological substance, gaseous-phase substance, and liquid-phase substance.

22. The method of claim 21, wherein each sensor has a sensing curve different from the other sensors.

23. A detection method comprising:
providing a plurality of transistor-based sensors, wherein each of the transistor-based sensors is different and each of the transistor-based sensors comprises a different gate electrode to detect a specific chemical or biological species in a detection medium; and
characterizing the chemical or biological species by a desorption temperature profile of the species on the gate electrode of each sensor;
operating the sensor by applying a thermal ramp over a particular temperature range; and collecting sensor data, the sensor data comprising: temperature reading data, sensor signal data, and radio frequency data associated with said sensor signal.

24. The method of claim 23, further comprising: locating the transistor-based sensors on one or more sensing units; and providing a radio frequency link to allow transmission of sensor signals from the sensors to a receiving unit, wherein the sensor signals correspond to thermal desorption spectra of the transistor-based sensors.

25. The method of claim 24, further comprising: comparing the sensor signals coming from a particular sensor with a data library to identify analytes in the detection medium.

26. The method of claim 23, wherein the transistor-based sensors comprise AlGaN/GaN high electron mobility transistors.

27. The method of claim 26, wherein each different gate electrode is made of a transition metal.

28. The method of claim 27, wherein the transition metal is selected from the group consisting of platinum, nickel, molybdenum, iridium, tungsten, palladium, ruthenium and rhodium.

29. A detection method comprising:
providing a plurality of transistor-based sensors, wherein each of the transistor-based sensors is different and adapted to detect and identify a specific chemical or biological species in a detection medium;
locating the transistor-based sensors on one or more sensing nodes;
selecting one between i) operating each sensor at a specific temperature, and ii) applying a thermal ramp over a certain temperature range; and
providing a radio frequency link to allow transmission of sensor signals from each of said one or more sensing nodes to a receiving unit.

* * * * *